United States Patent
Fang et al.

[11] Patent Number: 5,541,322
[45] Date of Patent: Jul. 30, 1996

[54] SYNTHESIS OF 6-AZAANDROSTENONES

[75] Inventors: Francis G. Fang, Durham; Matthew J. Sharp, Apex, both of N.C.

[73] Assignee: Glaxo Wellcome Inc., Research Triangle Park, N.C.

[21] Appl. No.: 323,404

[22] Filed: Oct. 14, 1994

[51] Int. Cl.$^6$ ............................................. C07D 221/18
[52] U.S. Cl. ................................... 546/42; 546/61
[58] Field of Search .......................... 546/42, 61

[56] References Cited

U.S. PATENT DOCUMENTS

| | | |
|---|---|---|
| 4,191,759 | 3/1980 | Johnston et al. . |
| 4,220,775 | 9/1980 | Rasmusson et al. . |
| 4,317,817 | 3/1982 | Blohm et al. . |
| 4,361,578 | 11/1982 | Alig et al. . |
| 4,377,584 | 3/1983 | Rasmusson et al. . |
| 4,814,324 | 3/1989 | Borris et al. . |
| 4,882,319 | 11/1989 | Holt et al. . |
| 4,888,336 | 12/1989 | Holt et al. . |
| 4,910,226 | 3/1990 | Holt et al. . |
| 4,937,237 | 6/1990 | Holt et al. . |
| 4,954,446 | 9/1990 | Holt et al. . |
| 4,966,897 | 10/1990 | Angelastro et al. . |
| 4,966,898 | 10/1990 | Angelastro et al. . |
| 5,017,568 | 5/1991 | Holt et al. . |
| 5,041,433 | 8/1991 | Holt et al. . |
| 5,061,801 | 10/1991 | Williams et al. . |
| 5,061,802 | 10/1991 | Steinberg et al. . |
| 5,061,803 | 10/1991 | Williams . |
| 5,098,908 | 3/1992 | Steinberg et al. . |
| 5,110,939 | 5/1992 | Holt et al. . |
| 5,278,159 | 1/1994 | Bakashi et al. . |
| 5,318,961 | 6/1994 | Weintraub et al. . |
| 5,342,948 | 8/1994 | Panzeri et al. . |
| 5,380,728 | 1/1995 | Rasmusson . |
| 5,438,061 | 8/1995 | Bergman et al. ............... 546/61 X |

FOREIGN PATENT DOCUMENTS

| | | |
|---|---|---|
| 004949A1 | 4/1979 | European Pat. Off. . |
| 052799A1 | 10/1981 | European Pat. Off. . |
| 314199A1 | 2/1985 | European Pat. Off. . |
| 155096A2 | 2/1985 | European Pat. Off. . |
| 200859A1 | 2/1986 | European Pat. Off. . |
| 271219A1 | 11/1987 | European Pat. Off. . |
| 271220A1 | 11/1987 | European Pat. Off. . |
| 277002A2 | 1/1988 | European Pat. Off. . |
| 285382A2 | 3/1988 | European Pat. Off. . |
| 285383A2 | 3/1988 | European Pat. Off. . |
| 298652A2 | 6/1988 | European Pat. Off. . |
| 343954A2 | 5/1989 | European Pat. Off. . |
| 367502A1 | 10/1989 | European Pat. Off. . |
| 375351A1 | 12/1989 | European Pat. Off. . |
| 375345A1 | 12/1989 | European Pat. Off. . |
| 375349A1 | 12/1989 | European Pat. Off. . |
| 375347A1 | 12/1989 | European Pat. Off. . |
| 375344A1 | 12/1989 | European Pat. Off. . |
| 414529A2 | 8/1990 | European Pat. Off. . |
| 414490A2 | 8/1990 | European Pat. Off. . |
| 414491A2 | 8/1990 | European Pat. Off. . |
| 427434A2 | 10/1990 | European Pat. Off. . |
| 428366A2 | 11/1990 | European Pat. Off. . |
| 435321A2 | 12/1990 | European Pat. Off. . |
| 462661A2 | 6/1991 | European Pat. Off. . |
| 462665A2 | 6/1991 | European Pat. Off. . |
| 462668A2 | 6/1991 | European Pat. Off. . |
| 462664A2 | 6/1991 | European Pat. Off. . |
| 462662A2 | 6/1991 | European Pat. Off. . |
| 469548A2 | 7/1991 | European Pat. Off. . |
| 469547A2 | 7/1991 | European Pat. Off. . |
| 473226A2 | 8/1991 | European Pat. Off. . |
| 473225A2 | 8/1991 | European Pat. Off. . |
| 478066A2 | 9/1991 | European Pat. Off. . |
| 484094A2 | 10/1991 | European Pat. Off. . |
| 5-170789 | 12/1991 | Japan . |
| WO91/12261 | 8/1991 | WIPO . |
| WO92/16213 | 10/1992 | WIPO . |

(List continued on next page.)

OTHER PUBLICATIONS

Ahmad, M. S. et al., "Beckmann Rearrangement of Some Steroid α–Hydroxy Ring B Ketoximes: 5–Oxo 5,6–Seco Nitriles," *Aust. J. Chem.*, 27, pp. 1537–1543, 1974.

Hsia, S. L. and Voigt, W., "Inhibition of Dihydrotestosterone Formation: An Effective Means of Blocking Androgen Action in Hamster Sebaceous Gland," *Journal of Investigative Dermatology*, 62, No. 3, pp. 224–227, 1974.

(List continued on next page.)

*Primary Examiner*—Fiona T. Powers
*Attorney, Agent, or Firm*—Charles E. Dadswell; Robert H. Brink

[57] ABSTRACT

A process of providing novel compounds of Formula (I), that are useful as 6-azaandrostenone testosterone 5-alpha-reductase inhibitors, from commercially available compounds of Formula (II)

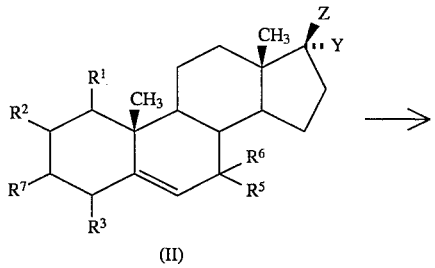

(II)

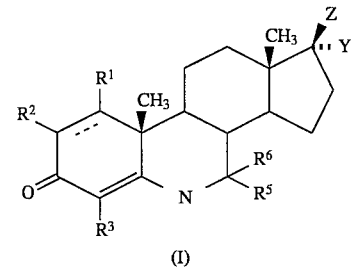

(I)

wherein the substituents are as defined in the specification, and the pharmaceutically acceptable salts and solvates thereof.

7 Claims, No Drawings

FOREIGN PATENT DOCUMENTS

| | | |
|---|---|---|
| WO92/18132 | 10/1992 | WIPO . |
| WO92/16233 | 10/1992 | WIPO . |
| WO93/13124 | 7/1993 | WIPO . |
| WO93/23051 | 11/1993 | WIPO . |
| WO93/23041 | 11/1993 | WIPO . |
| WO93/23040 | 11/1993 | WIPO . |
| WO93/23420 | 11/1993 | WIPO . |
| WO93/23419 | 11/1993 | WIPO . |
| WO93/23042 | 11/1993 | WIPO . |
| WO93/23038 | 11/1993 | WIPO . |
| WO93/23039 | 11/1993 | WIPO . |
| WO93/23048 | 11/1993 | WIPO . |
| WO93/23053 | 11/1993 | WIPO . |
| WO93/23050 | 11/1993 | WIPO . |
| WO94/03476 | 2/1994 | WIPO . |
| WO94/03475 | 2/1994 | WIPO . |
| WO94/07861 | 4/1994 | WIPO . |
| WO94/07909 | 4/1994 | WIPO . |
| WO94/11386 | 5/1994 | WIPO . |
| WO94/11004 | 5/1994 | WIPO . |
| WO94/14833 | 7/1994 | WIPO . |
| WO95/02607 | 1/1995 | WIPO . |

OTHER PUBLICATIONS

Holt, D. A., et al., "Steroidal A Ring Aryl Carboxylic Acids: A New Class of Steroid 5α–Reductase Inhibitors," *J. Med. Chem.*, 33, pp. 937–942, 1990.

Rasmusson, G. H., et al., "Azasteroids as Inhibitors of Rat Prostatic 5α–Reductase," *J. Med. Chem.*, 27, No. 12, pp. 1690–1701, 1984.

Liang, T., et al., "Biochemical and Biological Studies with 4–AZA–Steroidal 5α–Reductase Inhibitors," *J. Steroid Biochem.*, 19, No. 1, pp. 385–390, 1983.

House, H. O., "The Alkylation of Active Methylene Compounds," *Modern Synthetic Reactions*, 2d edition, pp. 492–570, The Benjamin/Cummings Publishing Co., 1972.

Rosini, G. and Medici, A., "Cleavage of α–Hydroxy–ketoximes Under Mild Conditions Using Phosphonitrile Dichloride," *Communications*, pp. 665–666, Oct. 1975.

Hugl, H. and Zbiral, E., "Umsetzungen Von $\Delta^5$–Steroidolefinen Mit Pb(OAc)$_{4-n}$(N$_3$)$_n^1$," *Tetrahedron*, 29, pp. 759–767, 1973.

Lazbin, I. M. and Koser, G. F., "Direct Conversion of Aliphatic Carboxamides to Alkylammonium Tosylates with [Hydroxy(tosyloxy)iodo]benzene," *J. Org. Chem.*, 51, No. 14, pp. 2669–2671, 1986.

Zbiral, E., et al., "Transferreaktionen Mit Hilfe Von Pb–I–V–Acetat—IV[1]," *Tetrahedron*, 26, pp. 1427–1434, 1970.

Zbiral, E. and Nestler, G., "Transferraktionen Mit Hilfe Von Phenyl–Jodosoacetatl[1]" *Tetrahedron*, 26, pp. 2945–2951, 1970.

Lettre, H., et al., "Verbesserung der Darstellung von 6–Aza–steroiden," *Liebigs Ann. Chem.* 703, pp. 147–151, 1967.

Feiser, L. F. and Rajagopalan, S., "Selective Oxidation with N–Bromosuccinimide," Converse Memorial Laboratory, Cambridge 38, Massachusetts, Jun. 1949.

Shoppee, C. W. and Roy, S. K., "Beckmann Rearrangement of Some α–Hydroxy–ketoximes," Dept. of Organic Chemistry, University of Sydney, Sydney, N.S.W., Australia, Dec. 1962.

Onda, M. and Takeuchi, K., "Alumina–Induced Reactions of Steroidal Oxime Acetates," *Chem. Pharm. Bull.*, 21, No. 6, pp. 1287–1290, 1973.

Staunton, J. and Eisenbraun, E. J., "3β–Acetoxyetienic Acid," *Organic Syntheses*, pp. 8–11, 1973.

Suzuki, M., et al., "Palladium(0)–Catalyzed Reaction of α,β–Ketones Leading to β–Diketones," *Journal of the American Chemical Society*, 102, No. 6, pp. 2095–2096, Mar. 12, 1980.

Wallis, E. S. and Lane, J. F., "The Hoffmann Reaction," *Organic Reactions*, Chapter 7, Krieger Publishing Company, Malabar, Florida, 1975.

Frye, S. V., et al., "6–Azasteroids: Potent Dual Inhibitors of Human Type 1 and 2 Steroid 5α–Reductase," *Journal of Medicinal Chemistry*, 36, No. 26, pp. 4313–4315, 1993.

Frye, S. V., "6–Azasteroids: Structure–Activity Relationships for Inhibition of Type 1 and 2 Human 5α–reductase and Human Adrenal 3β–Hydroxy–$\Delta^5$–steroid Dehydrogenase/3–Keto–$\Delta^5$–steroid Isomerase," (full paper corresponding to reference CS), 1993.

Petrow, V., et al., "6–Methylene–4–Pregnen–3–Ones as Irreversible Inhibitors of Rat Prostatic $\Delta^4$–3 Ketosteroid 5α–Reductase," *Steroids*, 38, No. 2, pp. 121–140, 1981.

Robaire, B. et al., "Selective Inhibition of Rat Epididymal Steroid $\Delta^4$5α–Reductase by Conjugated Allenic 3–Oxo–5, 10–Secosteroids," *Jrnl. of Steroid Biochemistry*, 8, pp. 307–310, 1977.

Imperato–McGinley, J. and Gautier, T., "Inherited 5α–Reductase Deficiency in Man," *TIG*, pp. 130–133, May 1986.

Brooks, J. R., et al., "5α–Reductase Inhibitory and Anti––Androgenic Activities of Some 4–Azasteroids in the Rat," *Steroids*, 47, pp. 1–19, Jan. 1986.

Brown, L., et al., "The Synthesis of Some Cholesterol Derivatives as Probes for Mechanisms of Cholesterol Metabolism," *J. Chem. Soc.*, pp. 595–599, 1987.

Rasmusson, G. H., et al., "Steroids: Structure–Activity Relationships for Inhibition of 5α–Reductase and Androgen Receptor Binding," *J. Med. Chem*, 29, pp. 2298–2315, 1986.

Stoner, E., "The Clinical Development of a 5α–Reductase Inhibitor, Finasteride," *J. Steroid Biochem. Molec. Biol.*, 37, No. 3, pp. 375–378, 1990.

van Velthuysen, J. A., et al., "Synthesis of (±)–N–Methyl–6–aza–8(14)–dehydro–19–nortestosterone," *Tetrahedron Letters*, 27, pp. 3081–3086, 1966.

Bhattacharya, A., et al., "Acylimidazolides as Versatile Synthetic Intermediates for the Preparation of Sterically Congested Amides and Ketones: A Practical Synthesis of Proscar," *Synthetic Communications*, 30, No. 17, pp. 2683–2690, 1990.

Jones, D. R., et al., "Origin and Structure of Benign Prostatic Hyperplasia," *British Journal of Urology*, 66, pp. 506–508, 1990.

Kutney, J. P. and Johnson, R. A., "Synthesis of 6–Aza–Steroids: A Novel Class of Steroidal Hormones," *Chemistry and Industry*, pp. 1713–1714, Oct. 1961.

Speckamp, W. N., et al., "Synthesis of N–Methyl–and N–Ethyl–6–Aza–8(14)–Dehydroestrone Methyl Ether," *Tetrahedron*, 24, pp. 5881–5891, 1968.

Jacobs, T. L. and Brownfield, R. B., "The Introduction of Oxygen and Nitrogen into the B Ring of the Steroid Nucleus," pp. 4033–4039, Aug. 1960.

Kutney, J. P., et al., "Synthesis of Ring A–Oxygenated 6–Aza Steroids," *Tetrahedron*, 24, pp. 845–857, 1968.

Sampson, W. J., et al., "The Effects of 6–Azacholest–4–en–3β–ol–7–one, an inhibitor of Cholesterol 7–α–Hydroxylase, on Cholesterol Metabolism and Bile Acid Synthesis in Primary Cultures of Rat Hepatocytes," *Biochimica et Biophysica Acta*, 960, pp. 268–274, 1988.

Kutney, J. P., "Synthesis of 6–Aza Steroids—A Novel Class of Azaandrostane Analogues," *Canadian J. of Chem.*, 41, pp. 613–619, 1963.

Speckamp, W. N., et al., "Synthesis of N–Methyl–6–Aza–8(14)–Dehydro–19–Nor–Testosterone," *Tetrahedron*, 24, pp. 5893–5898, 1968.

Imperato–McGinley, J., et al., "Androgens and the Evolution of Male–Gender Identity Among Male Pseudohermaphrodites with 5α–Reductase Deficiency," *The New England J. of Med.*, 300, No. 22, pp. 1233–1237, 1979.

Holt, D. A., et al., "Inhibition of Steroid 5α–Reductase by 3–Nitrosteroids: Synthesis, Mechanism of Inhibition, and In Vivo Activity," *Bioorganic & Medicinal Chem. Letters*, 1, No. 1, pp. 27–32, 1991.

Holt, D. A., et al., "Synthesis of a Steroidal A Ring Aromatic Sulfonic Acid as an Inhibitor of Steroid 5α–Reductase," Steroids, 56, pp. 4–7, 1991.

Levy, M. A., et al., "Inhibition of Rat Liver Steroid 5α–Reductase by 3–Androstene–3 Carboxylic Acids: Mechanism of Enzyme–Inhibitor Interaction," *Biochemistry*, 29, No. 11, pp. 2815–2824, 1990.

Dupuy, G. M., et al., "Steroidal Inhibitors of Prostatic 5α–Reductase: Structure–Activity Relationships," *Journal of Steroid Biochemistry*, 9, pp. 1043–1047, 1978.

Metcalf, B. W., "Potent Inhibition of Human Steroid 5α–Reductase (EC 1.3.1.30) by 3–Androstene–3–Carboxylic Acids," *Bioorganic Chemistry*, 17, pp. 372–376, 1989.

Andersson, S., et al., "Deletion of Steroid 5α–Reductase 2 Gene in Male Pseudohermaphroditism," *Nature*, 354, pp. 159–161, 1991.

Thigpen, A. E., et al., "Molecular Genetics of Steroid 5α–Reductase 2 Deficiency," *J. Clin. Invest.*, 90, pp. 799–809, 1992.

Thigpen, A. E., et al., "Brief Report: The Molecular Basis of Steroid 5α–Reductase Deficiency in a Large Dominican Kindred," *New England Jrnl. of Med.*, 327, No. 17, pp. 1216–1219, 1992.

Jenkins, E. P., "Genetic and Pharmacological Evidence for More Than One Human Steroid 5α–Reductase," *J. Clin. Invest.*, 89, pp. 293–300, 1992.

Dave, V., et al., "Resolution of Conflicting Migratory Reports in Ring Expansion of 3–Keto Steroids to Oxygen and Nitrogen," *Canadian J. Chem.*, 58, pp. 2666–2678, 1980.

Kobayashi, M., et al., "Reaction Products of 4–Aza–and 4–Methyl–4–azacholest–5–en–3–one with Nitrous Acid," *Chem. Pharm. Bull.*, 4, No. 20, pp. 789–793, 1972.

Narayanan, C. R., et al., "A Novel Reaction of Nitric Acid with Steroids," *Tetrahedron Letters*, No. 54, pp. 4703–4705, 1970.

SYNTHESIS OF 6-AZAANDROSTENONES

The present Invention relates to novel chemical intermediates and a novel chemical synthesis for the preparation of 6-azaandrostenones that are useful as testosterone 5-alpha-reductase inhibitors.

BACKGROUND OF INVENTION

Because of their valuable therapeutic potential, testosterone 5-alpha-reductase inhibitors have been the subject of active research worldwide and have been disclosed in numerous publications, United States and International patents and International patent applications, for example see, Hsia, S. and Voight, W., *J. Invest. Derm.*, 62, 224 (1973); Liang, T., et al., *J. Steroid Biochem.*, 19, 395 (1983); Holt, D., *J. Med. Chem.*, 33, 937 (1990); U.S. Pat. No. 4,377,584, to Rasmusson et al., issued Mar. 22, 1983, U.S. Pat. No. 5,017,568, to Holt et al., issued May 21, 1991, World patent applications WO 93/13124, filed by Glaxo Inc., and entitled, Inhibitors of 5-Alpha-Testosterone Reductase and WO 94/14833, field by Glaxo Inc., and entitled, Substituted 6-Azaandrostenones.

Previous methods used in the preparation of 6-azaandrostenones require the use of hazardous azide intermediates, extensive use of protecting groups which increase the number of synthetic steps, and the use of toxic heavy metal oxidants, for example see; Lettre, H., et al., *Liebigs Ann. Chem* 703, 147, (1967) and World Patent Application WO 93/13124, filed by Glaxo Inc., and entitled, Inhibitors of 5-Alpha-Testosterone Reductase. The present Invention provides a novel and efficient method for the preparation of useful intermediates, and 6-azaandrostenones of Formula (I) from commercially available compounds of Formula (II). The processes of the present Invention avoid the use of hazardous intermediates, and reagents, and are thus amenable to synthesis on a commercial scale.

SUMMARY OF THE INVENTION

One aspect of the present Invention is a process of providing novel 6-azaandrostenone compounds of Formula (I), that are useful as testosterone 5-alpha-reductase inhibitors, from commercially available compounds of Formula (II),

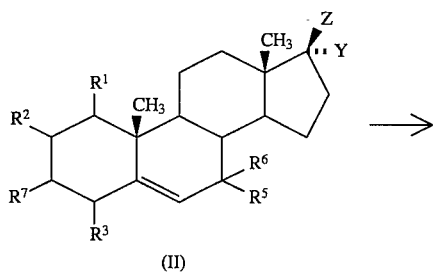

(II)

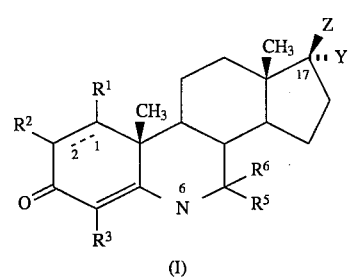

(I)

wherein:

$R^1$ and $R^2$ represent;
  i) independently H or alkyl and the bond between carbons 1 and 2 is a single bond or a double bond, or
  ii) taken together are a —$CH_2$— group to form a cyclopropane ring, and the bond between the carbons bearing 1 and 2 is a single bond, provided however, in compounds of Formula (II);
    R1 and R2 represent; independently H or alkyl or taken together are a —$CH_2$—group to form a cyclopropane ring;

$R^3$ represents H, —$Alk^1$—H optionally substituted with one or more halogen atoms, cycloalkyl, cycloalkylalkyl, halogen, —$(Alk^1)_n$—$CO_2$H, —$(Alk^1)_n$—$CO_2R^8$, —$(Alk^1)_n$—$Ar^1$, —$(Alk^1)_n$—$CONR^9R^{10}$, —$(Alk^1)_n$—$NR^9R^{10}$, —$(Alk^1)_n$—$S(O)_rR^8$, —$(Alk^1)_n$—CN, —$(Alk^1)$—OH, or —$(Alk^1)_n$—$OR^8$;

wherein:
  $Alk^1$ represents alkylene, alkenylene or alkynylene;
  n represents 0 or 1;
  r represents 0, 1 or 2;

$R^8$ represents —$Alk^1$—H, —$(Alk^1)_n$-$Ar^1$ or cycloalkyl;
wherein:
  —$Ar^1$ represents an aryl or heteraryl group of 6 to 14 atoms;

$R^9$ and $R^{10}$ represent independently H, —$Alk^1$—H or cycloalkyl;

Y represents H or hydroxy;

Z represents, —$(Alk^2)_n$—$COR^{11}$, —$(Alk^2)_n$—$CO_2R^{11}$, —$(Alk^2)_n$—CO-thiopyridinyl or —$(Alk^2)_n$—$CONR^{12}R^{13}$, wherein
  $Alk^2$ represents, $(C_{2-12})$ alkylene, $(C_{2-12})$ alkenylene or $(C_{2-12})$ alkynylene;

$R^{11}$ represents H, —$Alk^1$—H, cycloalkyl or adamantyl;

$R^{12}$ and $R^{13}$ represent,
  i) independently, H, —$Alk^2$—H, cycloalkyl, alkoxy, adamantyl, —$Ar^1$, —$Ar^1$-alkyl-perhaloalkyl, benzyl, diphenylmethyl, triphenylmethyl or —$(Alk^1)_n$-norbornyl; or
  ii) taken together with the linking nitrogen to form a 4 to 8 atom heterocyclic group

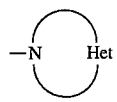

wherein:
  Het represents —O—, —$CH_2$—, —$S(O)_r$—, —NH— or —$N(Alk^1$—H)—; optionally substituted with one or more alkyl groups;

$R^5$ and $R^6$ represent H or alkyl;

$R^7$ represents hydroxy, alkoxy, halogen or $OCOR^{14}$,
wherein:
  $R^{14}$ represents H, alkyl, aryl or heteroaryl, and the pharmaceutically acceptable salts and solvate thereof.

In addition to a process for manufacturing the compounds of Formula (I), another aspect of the present Invention includes various intermediates useful in producing the compounds of Formula (I). Other aspects and advantages of the present Invention will become apparent from a review of the detailed description below.

DETAILED DESCRIPTION OF THE INVENTION

The term "alkyl" as used herein means, a linear or branched alkyl group with from 1 to about 15 carbon atoms, such as, but not limited to, methyl, ethyl, propyl, isopropyl, n-butyl, tert-butyl, hexyl, octyl, nonyl, decyl and dodecyl. The terms "cyclic" or "cyclo" as used herein mean alicyclic, aromatic or heterocyclic. The term "alkylene" as used herein means, a linear or branched chain saturated hydrocarbon group with from 1 to about 15 carbon atoms. The term "alkenylene" as used herein means, a linear or branched hydrocarbon chain containing one or more double bonds with from 2 to about 15 carbon atoms. The term "alkynylene" as used herein means, a linear or branched hydrocarbon chain containing one or more triple bonds with from 2 to about 15 carbon atoms. The term "alkoxy" as used herein means, an alkyl group, attached through an oxygen atom to the parent molecular subunit, such as, but not limited to, methoxy, ethoxy, propoxy, butoxy, pentoxy and hexoxy. The term "aryl" as used herein includes for example phenyl, naphthyl, and phenanthryl. The term "heteroaryl" as used herein includes such as pyridinyl, pyrimidinyl, furanyl, pyrollyl and thiophenyl. The terms "halo" and "halogen" as used herein refer to a substituent which may be fluoro, chloro, bromo, or iodo. The term "perhalo" as used herein means a substituent completely substituted with halogens. The term "ambient temperature" as used herein means from about 20° C. to about 30° C.

Compounds of the present Invention have one or more asymmetric carbon atoms that form enantiomeric arrangements, i.e., "R" and "S" configurations. The present Invention includes all enantiomeric forms and any combinations of these forms. For simplicity, where no specific configuration is depicted in the structural Formulas, it is to be understood that both enantiomeric forms and mixtures thereof are represented. Unless noted otherwise, the nomenclature convention, "(R)" and "(S)" denote essentially optically pure R and S enantiomers respectively. Relative stereochemistry is indicated by broad lines (β-bonds, coming out of the plane of the paper) and dotted or slashed lines (α-bonds, going behind the plane of the paper). Also included in the present Invention are other forms of the compounds including: solvates, hydrates, various polymorphs and the like.

Protecting groups used in the preparation of compounds of Formula (I) are used in the conventional manner. Conventional amino protecting groups include, but are not limited to, aralkyl groups such as benzyl, diphenylmethyl and triphenylmethyl groups or acyl groups such as N-benzyloxycarbonyl or t-butoxycarbonyl. Hydroxy groups may be protected by groups including, but not limited to, aralkyl groups, such as benzyl, diphenylmethyl or triphenylmethyl groups, acyl groups such as acetyl, silicon protecting groups such as trimethylsilyl or t-butyl dimethylsilyl or tetrahydropyran derivatives.

Removal of any protecting groups utilized may be achieved by conventional procedures. For example, an aralkyl group such as benzyl may be cleaved by hydrogenolysis in the presence of a catalyst (e.g. palladium on charcoal). An acyl group such as N-benzyloxycarbonyl may be removed by hydrolysis with, for example, hydrogen bromide in acetic acid or by a reduction reaction such as catalytic hydrogenation. Silicon protecting groups may be removed, for example, by treatment with fluoride ion or by hydrolysis under acidic conditions. Tetrahydropyran groups may be cleaved by hydrolysis under acidic conditions. For additional information on protecting groups see: *Protective Groups in Organic Chemistry* Ed. J. F. W. McOmie (Plenum Press 1973) or *Protective Groups in Organic Synthesis*, Theodora W. Greene (John Wiley and Sons 1981), both incorporated herein by reference.

Acceptable salts include, but are not limited to acid addition salts formed with inorganic acids such as hydrochloride, sulfate, phosphate, diphosphate, hydrobromide and nitrate or salts with organic acids such as acetate, malate, maleate, fumarate, tartrate, succinate, citrate, lactate, methanesulfonate, p-toluenesulfonate, palmoate, salicylate, oxalate and stearate when the compounds of formula (I) bear a basic substituent such as an amino group. When the compounds of formula (I) bear an acidic substituent, such as a carboxylic acid group, acceptable salts include, but are not limited to salts formed from organic bases such as ammonia and amines, e.g., diethylamine, or inorganic bases, such as alkaline metal or alkaline earth hydroxides, carbonates or bicarbonates, e.g., sodium hydroxide, potassium bicarbonate, calcium hydroxide, and magnesium carbonate. For further examples of acceptable salts see, *Pharmaceutical Salts*, J. Pharm. Sci., 66(1), 1 (1977), incorporated herein by reference.

One aspect of the present Invention provides for a total synthesis for the preparation of compounds of Formula (I) from commercially available compounds of Formula (II) as is schematically represented by the following overview reaction sequence exemplified in Scheme A wherein $R^4$ represents alkyl.

Scheme A

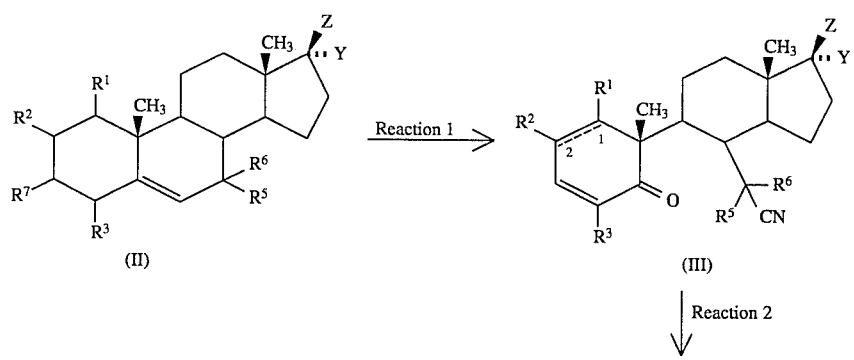

-continued
Scheme A

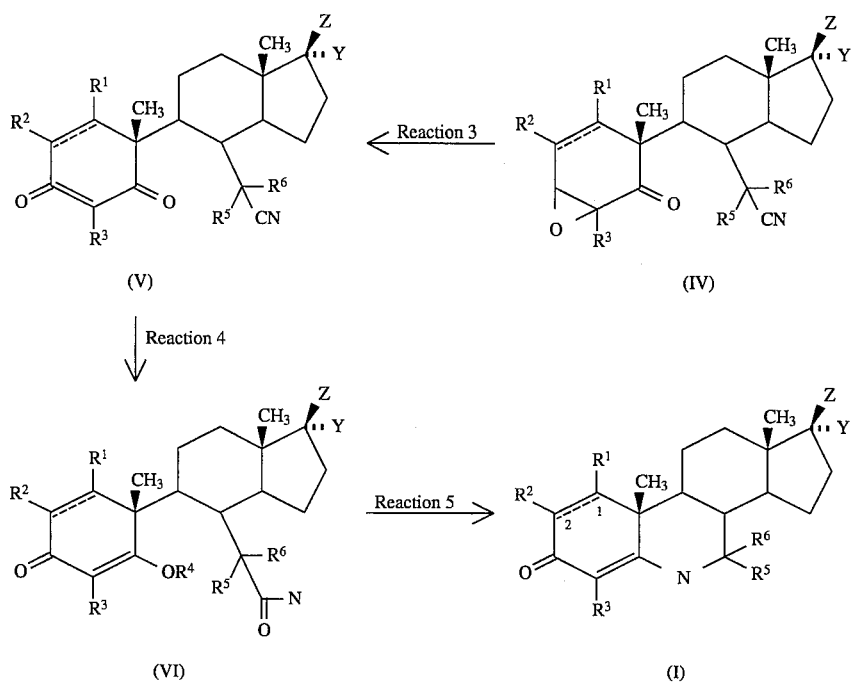

Reacting compounds of Formula (II) with a nitrosating agent yields compounds of Formula (III). Oxidizing the enone functionality in compounds of Formula (III) affords the epoxides of Formula (IV). Rearranging the epoxides of Formula (IV) in the presence of a palladium (0) complex yields the compounds of Formula (V), and reacting compounds of Formula (V) with a strong acid in the presence of an alcohol yields the compounds of Formula (VI). Hofmann rearrangement converts the compounds of Formula (VI) to the 6-azaandrostenones of Formula (I). This reaction Scheme A will be further understood and each of the above reactions will be further described in the following reaction Schemes B to F.

Scheme B, below further defines and describes Reaction 1 from Scheme A wherein compounds of Formula (II) are converted to compounds of Formula (III) in either a single step or a multistep synthesis. Also produced in reaction Scheme B are compounds of Formula (IIIa) which are converted to compounds of Formula (V) in Scheme C.

Scheme B

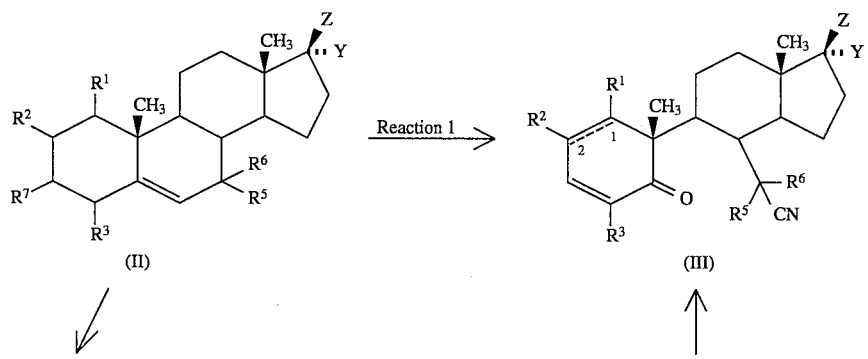

-continued
Scheme B

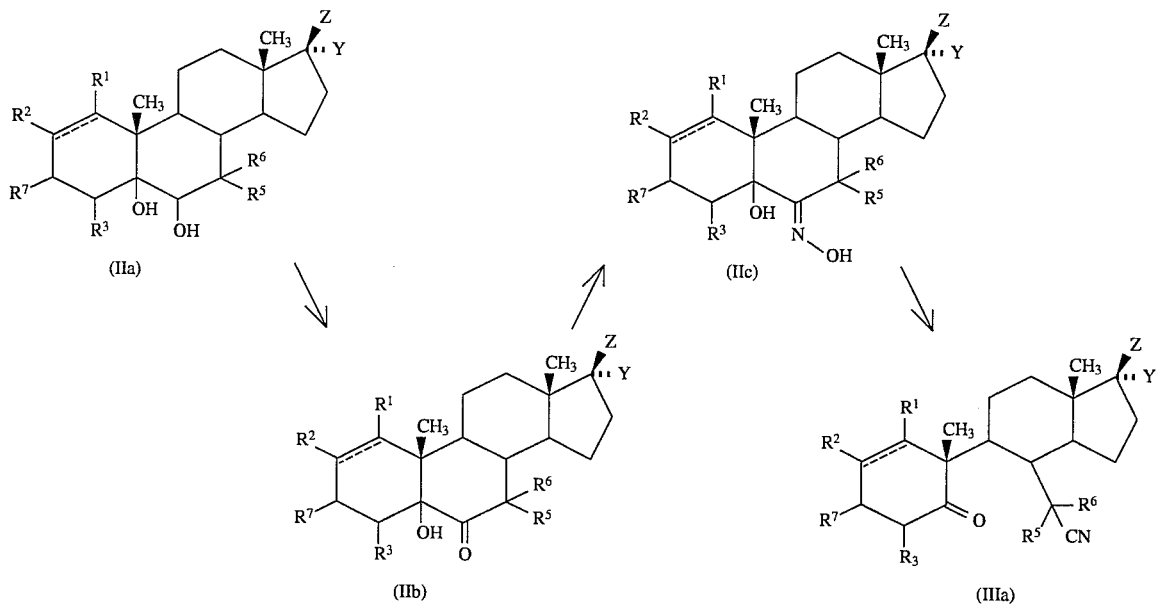

Conversion of the compounds of Formula (II), commercially available from various sources including: the Aldrich Chemical Company, Inc., 1001 West Saint Paul Avenue, Milwaukee, Wis. 53233, Steraloids, Inc. P.O. Box 310, Wilton, N.H. 03086 and Research Plus, Inc. P.O. Box 324, Bayonne, N.J. 07002, to the opened ring compounds of Formula (III) can be carried-out in a single step, as depicted by Reaction 1, in high yield by treatment with a nitrosating agent such as sodium nitrite and an organic or inorganic acid, such as, acetic acid with acetic anhydride, polyphosphoric acid, nitric acid or particuarly sulfuric acid or more particularly nitrosylsulfuric acid in a suitable polar aprotic solvent.

Alternatively, the conversion of compounds of Formula (II) to compounds of Formula (III) and/or compounds of Formula (IIIa) can be carried out in a stepwise manner as depicted in Scheme B. Compounds of Formula (II) can be oxidized to the compounds of Formula (IIa) by treatment with hydrogen peroxide and formic acid, followed by treatment with an aqueous base such as sodium hydroxide. The compounds of Formula (IIa) can be further oxidized to compounds of Formula (IIb) by treatment with N-bromosuccinimide in a mixture of a polar protic or polar aprotic solvent such as dioxane, methanol or diethylether and water. Alternatively, the compounds of Formula (II) can be directly oxidized to the compounds of Formula (IIb) by treatment with N-bromosuccinimide and acetic acid in acetone. These conditions are similar to those published by Fieser, L. F. et al., *J. Am. Chem. Soc.*, 3938, (1949). The compounds of Formula (IIb) can then be converted to the compounds of Formula (IIc) by treatment with hydroxylamine hydrochloride in the presence of sodium acetate in a polar protic solvent. These conditions are similar to those published by Shoppee, C. W. et al. *J. Chem. Soc.* 3774, (1963). The compounds of Formula (IIc) can be converted to the compounds of Formula (IIIa) by treatment with hexachlorocyclotriphosphazene in the presence of pyridine in a polar aprotic solvent such as tetrahydrofuran. These conditions are similar to those published by Rosini, G. et al. *Synthesis* 665, (1975). Treatment of compounds of Formula (IIc) under more usual Beckmann Fragmentation conditions, such as thionyl chloride affords a mixture of the compounds of Formula (IIIa) and the compounds of Formula (III). For additional information on the formation of 5-oxo-5, 6-seco nitriles from the Beckmann fragmentation of steroid hydroxy-oximes see: Ahmad, M. S. et al., Aust. *J. Chem.*, 27, 1537, (1974); Onda, et al., *Chem. Pharm. Bull.* 21, 1287, (1973). incorporated herein by reference.

Persons skilled in the art will quickly realize that during the herein described synthesis of 6-azaandrostenones, once compounds of Formula (III) have been synthesized that the substituent Z may be exchanged for other substituents, herein described, and the double bond between carbons 1 and 2 may be added, without detrimental effects on the remaining portion of the molecule or the remaining syntheses. Persons skilled in the art will also realize this is merely an example of one place in the syntheses this exchange or addition can be achieved and should not be construed as a limitation of the present Invention.

Scheme C, below further defines and describes Reactions 2 and 3 from Scheme A wherein compounds of Formula (III) are converted to compounds of Formula (V) through compounds of Formula (IV). Scheme C also defines and describes the conversion of the compounds of Formula (IIIa), from Scheme B, to the compounds of Formula (V).

Scheme C

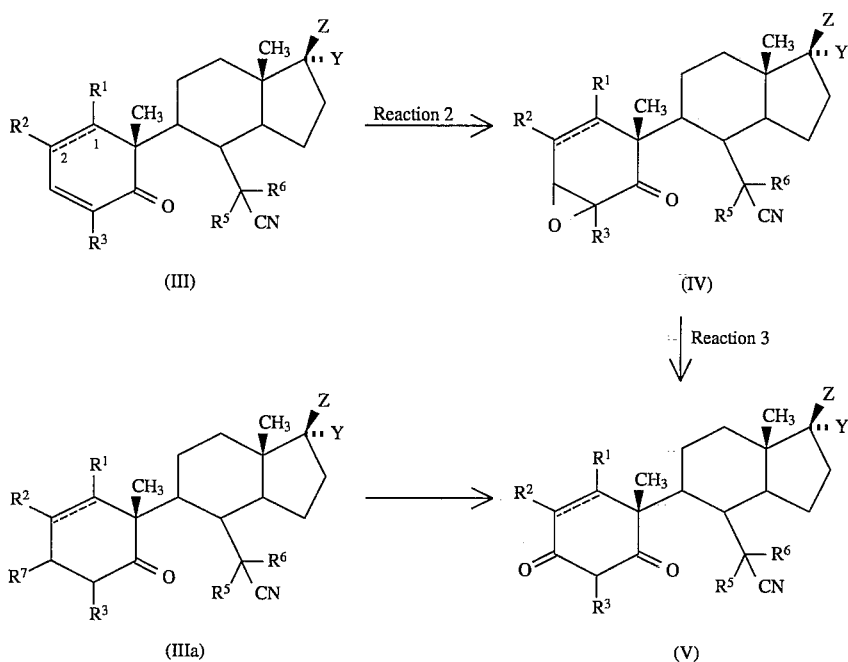

Oxidation of the compounds of Formula (III) with organic peroxides, such as tert-butyl hydroperoxide, or particularly hydrogen peroxide in the presence of a inorganic or amine bases such as, sodium bicarbonate, potassium carbonate, lithium hydroxide, potassium hydroxide, 1,8-diazabicyclo[5.4.0]undec-7-ene, N-benzyltrimethylammonium hydroxide and pyridine or particularly sodium hydroxide, in a polar protic or aprotic solvent affords the epoxides of Formula (IV) in an α to β ratio of approximately 7:1. A selective rearrangement of the α-epoxides of Formula (IV) with a palladium (0) catalyst such as di[1,2-bis(diphenylphosphino)ethane]palladium (0), bis(dibenzylideneacetone)palladium (0) or particularly tetrakis(triphenylphosphine) palladium (0) in the presence of a bidentate ligand such as 1,4-bis(diphenylphosphino)butane, 1,3-bis(diphenylphosphino)propane or particularly 1,2-bis(diphenylphosphino)ethane in a polar aprotic solvent affords the corresponding compounds of Formula (V). Alternatively, the compounds of Formula (V) can be prepared by oxidation of the compounds of Formula (IIIa) wherein $R^7$ represents hydroxy.

Persons skilled in the art will quickly realize that during the herein described synthesis of 6-oazaandrostenones, once compounds of Formula (V) have been synthesized that the substituent $R^3$ may be exchanged for other substituents, herein described, without detrimental effects on the remaining portion of the molecule or the remaining syntheses. Persons skilled in the art will also realize this is merely an example of one place in the syntheses this exchange can be achieved and should not be construed as a limitation of the present Invention.

Scheme D below, further defines and describes Reaction 4 from Scheme A wherein;

$R^4$ represents alkyl.

Compounds of Formula (V) are converted to compounds of Formula (VI) and (VIa). This transformation can be carried out in one step, or alternatively in two steps going through the intermediate compounds of Formula (VII).

Scheme D

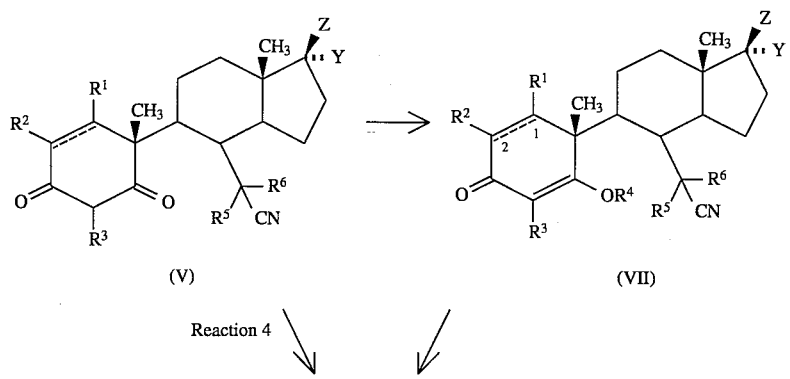

-continued
Scheme D

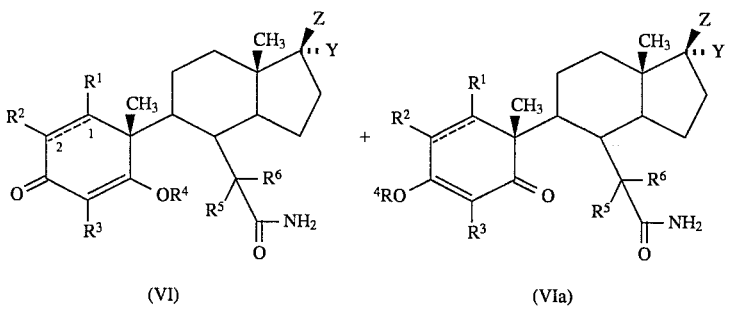

According to Scheme D, compounds of Formula (V) are reacted with a non-oxidizing anhydrous mineral acid such as hydrogen bromide or particularly hydrogen chloride in the presence of an alcohol of the Formula $R^4OH$ to afford a mixture of the compounds of Formula (VI) and (VIa). Alternatively, this transformation may be carried out in two separate steps: alkylating of compounds of Formula (V) with a trialkyl orthoformate of the Formula $HC(OR^4)_3$, such as, triethyl orthoformate, tripropyl orthoformate, triisopropyl orthoformate or particularly trimethyl orthoformate, optionally in an alcohol of the Formula $R^4OH$, wherein $R^4$ is the same for both the trialkyl orthoformate and the alcohol, in the presence of a catalytic amount of a non-oxidizing mineral or organic acid such as, methansulfonic acid, trifluoromethanesulfonic acid, camphorsulfonic acid and particularly p-toluenesulfonic acid to afford the compounds of Formula (VII) which can be converted to the mixture of compounds of Formula (VI) and (VIa) using the conditions described above.

Scheme E, below further defines and describes the synthesis of compounds of Formula (VIII) and the conversion of compounds of Formula (VIII) to 6-azaandrostenones of Formula (I) and Reaction 5 of Scheme A wherein compounds of Formula (VI) are converted to 6-azaandrostenones of Formula (I).

Scheme E

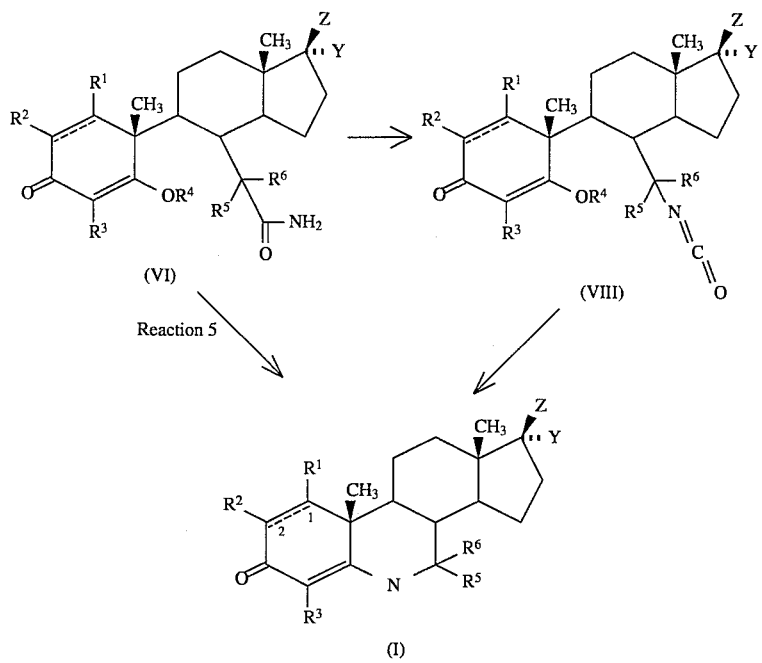

The conversion of compounds of Formula (VI) to compounds of Formula (I) is completed in a single step by treatment with suitable "Hofmann reagents" (Hofmann reagents as used herein refers to reagents that are able to effect a Hofmann rearrangement, see: Wallis et al. *Org. React.* 3, 267, (1946) incorporated herein by reference). For example, the treatment of compounds of Formula (VI) with bis(trifluoroacetoxy)iodobezene (see: Radhakrishna et al., *J. Org. Chem.* 44, 1746 (1979) incorporated herein by reference), sodium hypochlorite, sodium hypobromate or particularly hydroxy(tosyloxy)iodobezene (see: Lazbin, I. M. et al., *J. Org. Chem.* 151, 2669, (1986) incorporated herein by reference), in a mixture of a polar aprotic solvent such as acetonitrile and water at a temperature of from about 50° to about 100° C. Alternatively, the conversion of compounds of Formula (VI) to the compounds of Formula (I) may be carried out in two separate independent steps treating compounds of Formula (VI) as described above under anhydrous conditions affords the intermediate of Formula (VIII) which can be transformed to compounds of Formula (I) under hydrolytic conditions: treatment with a non-oxidizing mineral acid such as hydrochloric acid in a polar protic solvent at a temperature of from about 30° to about 100° C.

Scheme F, below further defines and describes the synthesis of 6-azaandrostenones of Formula (I) from compounds of Formula (VIa) through the intermediate compounds of Formula (IX).

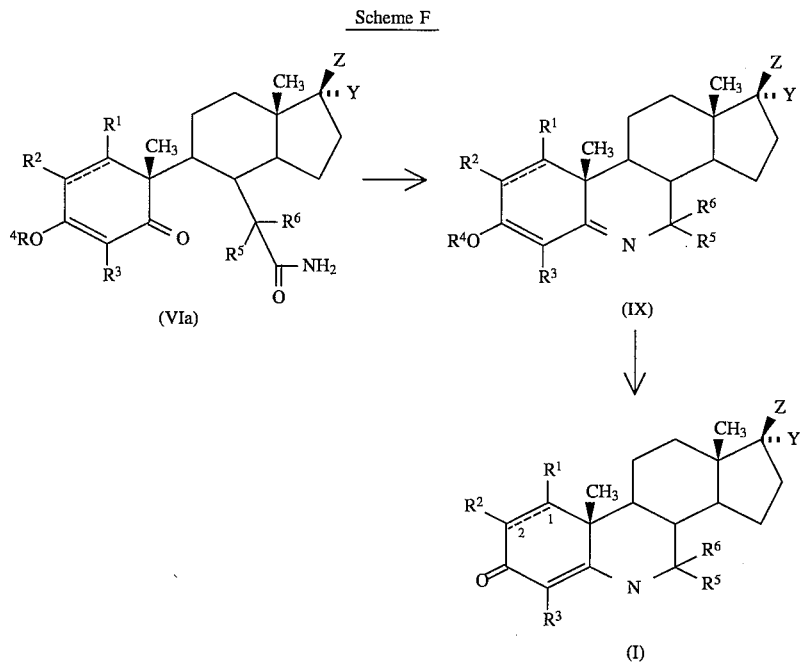

Scheme F

The conversion of compounds of Formula (VIa) to compounds of Formula (IX) is accomplished by treatment with suitable Hofmann reagents herein described. For example, treatment of compounds of Formula (VIa) with bis(trifluoroacetoxy)iodobezene, sodium hypochlorite, sodium hypobromate or particularly hydroxy(tosyloxy)iodobenzene, in a mixture of a polar aprotic solvent such as acetonitrile and water at a temperature of from about 50° to about 100° C. affords the compounds of Formula (IX). The conversion of the compounds of Formula (IX) to the 6-azaandrostenones of Formula (I) is carried out under hydrolytic conditions such as treatment with a mild acid such as Amberlyst® 15 ion-exchange resin, Dowex® 50 W ion-exchange resin or particularly silica gel in a suitable aprotic solvent such as toluene at a temperature of from about 50° to about 120° C.

A typical preparation of a 6-azaandrostenone of Formula (I) utilizing the process and intermediates of the present Invention is exemplified herein.

EXAMPLES

The following examples illustrate various aspects of the present Invention, but should not be construed as limitations. The symbols, conventions and nomenclature are consistent with those used in the contemporary chemical literature, such as the *Journal of the American Chemical Society*.

Unless otherwise noted all starting materials were obtained from commercial suppliers and used without further purification. All reactions involving oxygen or moisture-sensitive compounds were performed under a dry $N_2$ atmosphere. All reactions and chromatography fractions were analyzed by thin-layer chromatography on silica gel plates, visualized with UV light and $I_2$ stain.

Example 1

17β-Carbomethoxy-3β-acetoxy-5-androstene

To a mechanically stirred solution of 17β-carbomethoxy-3β-hydroxy-5-androstene (100 g, 0.30 mol), prepared as described in Rasmusson et al., *Journal of Medicinal Chemistry* 1984, 27, 1690, incorporated herein by reference, in pyridine (750 mL) in a 2 L 4-necked round bottom flask equipped with an addition funnel at ambient temperature is added acetic anhydride (130 mL, 1.38 mol). The resulting dark solution is stirred at ambient temperature for 18 h, transferred to an addition funnel, and added drop wise to 3 L of ice-water. The resulting precipitate is collected by filtration, washed with 2×1 L $H_2O$, and dried under vacuum to afford 17β-carbomethoxy-3β-acetoxy-5-androstene; $^1H$ NMR (400 MHz, $CDCl_3$) δ5.36 (br d, J=5.1 Hz, 1H), 4.59 (m, 1H), 3.67 (s, 3H), 2.37–2.29 (m, 3H), 2.20–2.08 (m, 1H), 2.03 (s, 3H), 2.02–1.97 (m, 2H), 1.90–1.38 (m, 10H), 1.34–1.21 (m, 2H), 1.18–1.05 m, 2H), 1.02 (s, 3H), 1.00–0.96 (m, 1H), 0.66 (s, 3H).

Example 2

17β-Carbomethoxy-6-nitrilo-5-oxo-5,6-secoandrost-3-ene

To a suspension of 17β-carbomethoxy-3β-acetoxy-5-androstene (70.66 g, 0.189 mol), produce as in example 1, in diethyl ether (1000 mL) in a 4-necked 3 L flask equipped with mechanical stirrer, J-Kem thermocouple, addition funnel, and nitrogen inlet at −10° C. is added nitrosyl sulfuric acid (115 mL, of a 40% solution in $H_2SO_4$). The addition is made drop wise at such a rate that the temperature of the reaction mixture did not rise above −8° C. After the addition is complete the cooling bath is removed and the mixture is allowed to warm to ambient temperature. After 18 h at ambient temperature, the resulting solution is cooled to 0° C.

and a 25% solution of KOH is added drop wise until basic (ca. 900 mL). The resulting mixture is filtered and the solids washed with 3×200 mL of diethyl ether. The filtrate is transferred to a separating funnel, the phases separated, and the aqueous layer extracted with 1×200 mL of diethyl ether. The combined organic layers are dried ($Na_2SO_4$) and concentrated to afford 17β-carbomethoxy-6-nitrilo-5-oxo-5,6-secoandrost-3-ene as an off white foam which is used in the next step without any further purification. $^1$H NMR (400 MHz, $CDCl_3$) δ6.75 (m, 1H), 5.91 (dd, J=9.9 and 1.8 Hz, 1H), 3.55 (s, 3H), 2.65 (dd, J=17.7 and 3.9 Hz, 1H), 2.35 (m, 1H), 2.32 (t, J=9.4 Hz, 1H), 2.19–1.88 (m, 6H), 1.80–1.35 (m, 7H), 1.30 (td, J=12.8 and 3.6 Hz, 1H), 1.13 (m, 1H), 0.94 (s, 3H), 0.56 (s, 3H); IR ($CHCl_3$) 3200, 2940, 1730, 1675, 1440 cm$^{-1}$.

Example 3

17β-Carbomethoxy-3α,4α-epoxy-6-nitrilo-5-oxo-5,6-secoandrostane
17β-Carbomethoxy-3β,4β-epoxy-6-nitrilo5-oxo-5,6-secoandrostane To a magnetically stirred solution of 17β-carbomethoxy-6-nitrilo-5-oxo-5,6 -secoandrost-3-ene (67.86 g), as prepared in example 2, in methanol (850 mL) at ambient temperature is added 1N NaOH (50 mL) followed by 30% $H_2O_2$ (500 mL). The resulting mixture is stirred at ambient temperature for 4 h, during which time crystals formed. Water 100 mL of is added. The resulting solids are collected by filtration and washed with $H_2O$ (2×100 mL). The crystalline product is air dried to afford a mixture of α and β epoxide stereoisomers (7:1 respectively by $^1$H NMR analysis). Characterization data for α epoxide: $^1$H NMR (400 MHz, $CDCl_3$) δ3.66 (s, 3H), 3.60 (br s, 1H), 3.23 (d, J=3.9 Hz, 1H), 2.72 (dd, J=17.6 and 3.8 Hz, 1H), 2.43 (t, J=9.14 Hz, 1H), 2.32 (dd, J=17.7 and 3.5 Hz, 1H), 2.26 (m, 1H), 2.23–1.52 (m, 12H), 1.35–1.23 (m, 3H), 1.16 (s, 3H), 0.69 (s, 3H); Anal. Calcd. for $C_{21}H_{29}NO_4$: C, 70.17; H, 8.18; N, 3.90. Found: C,70.15; H, 8.20; N, 3.84. Characterization data for β epoxide: $^1$H NMR (400 MHz, $CDCl_3$) δ3.60 (s, 3H), 3.53 (br s, 1H), 3.42 (d, J=3.3 Hz, 1H), 2.60 (dd, J=17.9 and 4.2 Hz, 1H), 2.36 (t, J=9.5 Hz, 1H), 2.10–1.32 (m, 18H), 0.93 (s, 3H), 0.60 (s, 3H), 0.60 (s, 3H).

Example 4

17β-Carbomethoxy-3,5-dioxo-6-nitrilo-5,6-secoandrostane

To a magnetically stirred solution of 17β-carbomethoxy-3α,4α-epoxy-6 -nitrilo-5-oxo-5,6-secoandrostane and 17β-carbomethoxy-3β,4β-epoxy-6-nitrilo-5-oxo-5,6-secoandrostane (30.0 g, 83.6 mmol, 7:1 mixture α:β), prepared as in example 3, 1,2-bis(diphenylphosphino)ethane (1.33 g, 3.34 mmol) in anhydrous THF (125 mL) under a nitrogen atmosphere is added tetrakis(triphenylphosphine)palladium (0) (3.90 g, 3.34 mmol). The resulting mixture is heated at reflux for 18 h then allowed to cool to ambient temperature and concentrated. The residue is filtered through a short plug of Florisil® using $CH_2Cl_2$ as eluent to afford 17β-carbomethoxy-3,5-dioxo-6-nitrilo-5,6-secoandrostane as an off-white foam which is used in the next step without any further purification. $^1$H NMR (400 MHz, $CDCl_3$. Characteristic signals only. This compound exists as a mixture of keto and enolic forms 10:1 respectively in $CDCl_3$ the characteristic signals of the enolic form are italicized) δ5.42 (s, 1H), 4.27 (d, J=17.3 Hz, 1H), 3.86 (m, 1H), 3.68 (s, 3H), 3.44 (dd, J=17.3 and 1.8 Hz, 1H), 3.22 (t, J=12.5 Hz, 1H), 2.81 (dd, J=12.6 and 5.0 Hz, 1H), 112 (s, 3H), 0.96 (s, 3H), 0.71 (s, 3H), 0.68 (s, 3H).

Example 5

17β-Carbomethoxy-5-methoxy-6-nitrilo-3oxo-5,6-secoandrost-4-ene

To a magnetically stirred solution of 17β-carbomethoxy-3,5-dioxo-6-nitrilo-5,6-secoandrostane (2.82 g), as prepared in example 4, and trimethylorthoformate (1.4 mL) in methanol (7.0 mL) under a nitrogen atmosphere at ambient temperature is added p-TsOH (15 mg). The resulting mixture is stirred at ambient temperature for 22 h, diluted with $CH_2CL_2$ (20 mL), washed with 1N NaOH (10 mL), dried over $Na_2SO_4$ and concentrated. Purification of the residue by silica gel column chromatography using hexane-ethyl acetate 2:1 as eluent affords 17β-carbomethoxy-5-methoxy-6-nitrilo-3-oxo-5,6-secoandrost-4-ene. $^1$H NMR (400 MHz, $CDCl_3$) δ5.38 (s, 1H), 3.72 (s, 3H), 3.67 (s, 3H), 2.98 (dd, J=17.7 and 3.8 Hz, 1H), 2.54 (m, 1H), 2.42 (t, J=9.3 Hz, 1H), 2.26 (m, 1H), 2.18–1.48 (m, 15H), 1.41 (td, J12.7 and 4.0 Hz, 1H), 1.26 (m, 1H), 1.07 (s, 3H), 0.67 (s, 3H).

Example 6

17β-Carbomethoxy-6-amido-3-methoxy-5-oxo-5,6-secoandrost-3-ene;
17β-carbomethoxy-6-amido-5-methoxy-3-oxo-5,6-secoandrost-4-ene A suspension of 17β-Carbomethoxy-3,5-dioxo-6-nitrilo-5,6-secoandrostane (5.00 g), as prepared in example 4, in diethylether-MeOH 3:1 (130 mL) is magnetically stirred at 0° C. HCl gas is bubbled through the mixture until it becomes saturated (ca 30 min). The resulting clear solution is allowed to warm to ambient temperature and stirred for 16 h and then concentrated in vacuo. The solid residue is dissolved in $CH_2Cl_2$ (125 mL) and 1N NaOH (125 mL) is added. The two phase mixture is rapidly stirred for 15 min, the phases separated, the aqueous layer is extracted with $CH_2Cl_2$ (50 mL), and the combined organic layers are dried over $Na_2SO_4$ and concentrated. The residue is purified by silica gel column chromatography using MeOH—$CHCl_3$ 20:1 as eluent to afford 17β-carbomethoxy-6-amido-5-methoxy-3-oxo-5,6-secoandrost-4-ene: $^1$H NMR (400 MHz, $CDCl_3$) δ5.53 (br s 1H), 5.48 (br s, 1H), 5.18 (s, 1H), 3.57 (s, 3H), 3.56 (s, 3H), 2.39 (dd, J=17.0 and 2.4 Hz, 1H), 2.23–2.25 (m, 3H), 1.95–2.18 (m, 4H), 1.81–1.87 (m, 2H), 1.60–1.78 (m, 3H), 1.17–1.27 (m, 5H), 1.29 (s, 3H), 0.58 (s, 3H) and 17β-carbomethoxy- 6-amido-3-methoxy-5-oxo-5,6-secoandrost-3-ene $^1$H NMR (400 MHz, $CDCl_3$) δ5.50 (br s, 1H), 5.95 (br s, 1H), 5.11 (s, 1H), 3.56 (s, 3H), 3.52 (s, 3H), 2.30–2.43 (m, 1H), 122–2.23 (m, 16H), 0.99 (s, 3H), 0.52 (s, 3H).

Example 7

17β-Carbomethoxy-6-isocyanato-5-methoxy-3-oxo-5,6-secoandrost-4-ene

A magnetically stirred mixture of 17β-carbomethoxy-6-amido-5-methoxy-3 -oxo-5,6-secoandrost-4-ene (18 mg, 0.046 mmol), as prepared in example 6, and PhI(OH)OTs (18 mg, 0.046 mmol) in $CH_3CN$ (0.25 mL) is heated under a nitrogen atmosphere at 75° C. for 12h. The resulting solution is allowed to cool to ambient temperature diluted with CH$_2$Cl$_2$ (10 mL), washed with 1N HCl (10 mL), followed by 1N NaOH (10 mL) and concentrated to yield 17β-carbomethoxy-6-isocyanato-5-methoxy-3-oxo-5,6-secoandrost-4-ene: $^1$H NMR (400 MHz, CDCl$_3$) δ5.76 (s, 1H), 4.24 (dd, J=12.5 and 4.6 Hz, 1H), 3.65 (s, 3H), 3.63 (m, 1H), 3.61 (s, 3H), 2.53 (t, J=12.1 Hz, 1H), 2.48–2.27 (m, 3H), 2.13–1.50 (m, 9H), 1.39–1.15 (m, 3H), 1.13 (s, 3H), (1.11–1.67 (m, 2H), 0.64 (s, 3H).

Example 8

17β-Carbomethoxy-3-methoxy-6-azaandrost-3,5-diene

A magnetically stirred suspension of 17β-carbomethoxy-6-amido-3-methoxy-5-oxo-5,6-secoandrost-3-ene (451 mg, 1.15 mmol), as prepared in example 6, and PhI(OH)OTs (475 mg, 1.21 mmol) in CH$_3$CN—H$_2$O 1:1 (5.6 mL) is heated under a nitrogen atmosphere for 15 h. The resulting solution is allowed to cool to ambient temperature, diluted with CH$_2$Cl$_2$ (20 mL), washed with 1N HCl (20 mL), followed by 1N NaOH (20 mL) and concentrated to afford 17β-carbomethoxy-3-methoxy-6-azaandrost-3,5-diene: $^1$H NMR (400 MHz, CDCl$_3$) δ6.35 (s, 1H), 3.83 (s, 3H), 3.77 (dd, J=6.2 and 16.6 Hz, 1H), 3.65 (s, 3H), 3.15 (dd, J=10.8 and 16.5 Hz, 1H), 2.55 (m, 1H), 2.43–1.24 (m, 15H), 1.22 (s, 3H), 0.68 (s, 3H); HRMS (EI+) 345.2304 (345.2304 Calcd for C$_{21}$H$_{31}$NO$_3$).

Example 9

17β-Carbomethoxy-6-azaandrost-4-en-3-one

A magnetically stirred suspension of 17β-carbomethoxy-6-amido-5-methoxy-3-oxo-5,6-secoandrost-4-ene (1.35 rag, 3.45 mmol), as prepared in example 6, and PhI(OH)OTs (1.42 mg, 3.62 mmol) in CH$_3$CN—H$_2$O 1:1 (16 mL) is heated under a nitrogen atmosphere for 2 h. The resulting solution is allowed to cool to ambient temperature, diluted with CH$_2$Cl$_2$ (75 mL), washed with 1N HCl (75 mL), followed by 1N NaOH (75 mL) and concentrated. The residue is recrystalized from acetone to afford 17β-carbomethoxy-6-azaandrost-4-en-3-one: $^1$H NMR (400 MHz, CDCl$_3$) δ5.45 (br s, 1H), 5.12 (s, 1H), 3.68 (s, 3H), 3.35 (dd, J=11.0 and 5.0 Hz, 1H), 2.87 (t, J=11 Hz, 1H), 2.25–2.51 (m, 3H), 1.58–2.23 (m, 9H), 1.56–1.72 (m, 3H), 1.12–1.50 (m, 6H), 1.29 (s, 3H), 0.72 (s, 3H).

Example 10

6-Nitrilo-5-oxo-5,6-secoandrost-3-en-17β-carboxylic acid

To a magnetically stirred solution of 17β-carbomethoxy-6-nitrilo-5-oxo-5,6-secoandrost-3-ene (1.37 g, 3.99 mmol), as prepared in example 2, in dioxane-H$_2$O 2:1 (15 mL) at ambient temperature under a nitrogen atmosphere, is added LiOH.H$_2$O (335 mg, 7.98 mmol). The resulting suspension is stirred at ambient temperature for 17 h, acidified with 1N HCl, and extracted with CHCl$_3$ (2×40 mL). The combined organic extracts are dried over Na$_2$SO$_4$ and concentrated to afford 6-nitrilo-5-oxo-5,6-secoandrost-3-en-17β-carboxylic acid that is used in the next step without any further purification: $^1$H NMR (400 MHz, CDCl$_3$) δ6.82 (m, 1H), 6.01 (dd, J=10.2 and 1.8 Hz, 1H), 2.74 (dd, J=17.8 and 3.7 Hz, 1H), 2.47–1.18 (m, 17H), 1.02 (s, 3H), 0.71 (s, 3H).

Example 11

17β-N-(2-t-butyl-5-trifluoromethyl)-phenyl-6-nitrilo-5-oxo-5,6-secoandrost-3-ene To a magnetically stirred solution of 6-nitrilo-5-oxo-5,6-secoandrost-3-en-17β-carboxylic acid (1.52 g, crude), as prepared in example 10, and pyridine (0.86 mL, 10.63 mmol) in toluene (30 mL) at 0° C. under a nitrogen atmosphere is added SOCl$_2$ (0.37 mL, 5.08 mmol). The resulting mixture is allowed to warm to ambient temperature, and stirred at this temperature for 2 h. To this mixture is added 2-t-butyl-5-trifluoromethylaniline (1.05 g, 4.85 mmol), that may be prepared as in WO 94/14833, filed by Glaxo Inc., and entitled, Substituted 6-Azaandrostenones, as a solution in toluene (5 mL), followed by DMAP (15 mg, 0.16 mmol). The resulting mixture is then heated at 85° C. for 18 h, allowed to cool to ambient temperature, and is washed with 1N HCl (30 mL) followed by 1N NaOH (30 mL), dried over Na$_2$SO$_4$ and concentrated. The residue is purified by silica gel column chromatography using hexanes-EtOAc 3:1 as eluent to afford 17β-N-(2-t-butyl-5-trifluoromethyl)-phenyl-6-nitrilo-5-oxo-5,6-secoandrost-3-ene: $^1$H NMR (400 MHz, CDCl$_3$) δ8.08 (s, 1H), 7.47 (d, J=8.4 Hz, 1H), 7.34 (d, J=8.3 Hz, 1H), 7.28 (s, 1H), 6.84 (m, 1H), 6.04 (dd, J=10.1 and 1.6 Hz, 1H), 2.80 (dd, J=17.8 and 3.8 Hz, 1H), 2.48–1.55 (m, 18H), 1.50 (td, J=12.3 and 3.3 Hz, 1H), 1.42 (s, 9H), 1.33 (m, 1H), 1.07 (s, 3H), 0.85 (s, 3H).

Example 12

17β-N-(2-t-Butyl-5-trifluoromethyl)-phenyl-3α,4α-epoxy-6-nitrilo-5-oxo-5,6-secoandrostane To a magnetically stirred mixture of 17β-N-(2-t-Butyl-5-trifluoromethyl)-phenyl-6-nitrilo-5-oxo-5,6-secoandrost-3-ene (1.23 g, 2.33 mmol), as prepared in example 11, in MeOH (30 mL) at ambient temperature is added 1N NaOH (0.60 mL) followed by 30% H$_2$O$_2$ (8.0 mL). The resulting mixture is stirred at ambient temperature for 1 h and H$_2$O (20 mL) is added drop wise. The resulting precipitate is collected by filtration, air-dried for 2 h and then dried under vacuum overnight to afford of 17β-N-(2-t-Butyl-5-trifluoromethyl)-phenyl-3α,4α-epoxy-6-nitrilo-5 -oxo-5,6-secoandrostane: $^1$H NMR (400 MHz, CDCl$_3$) δ8.16 (s, 1H), 7.48 (d, J=8.3 Hz, 1H), 7.34 (d, J=8.3 Hz, 1H), 7.21 (s, 1H), 3.61 (m, 1H), 3.26 (d, J=4.0 Hz, 1H), 2.73 (dd, J=17.6 and 4.0 Hz, 1H), 2.43–1.60 (m, 16H0, 1.44 (s, 9H), 1.40–1.31 (m, 1H), 1.19 (s, 3H), 0.89 (s, 3H). Anal. Calcd. for C$_{31}$H$_{39}$N$_2$O$_3$F$_3$: C, 68.36; H, 7.22; N, 5.14. Found: C, 68.40; H, 7.27; N, 5.06.

Example 13

17β-N-(2-t-Butyl-5-trifluoromethyl)-phenyl-3,5-dioxo-6-nitrilo-5,6-secoandrostane To a magnetically stirred solution of 17β-N-(2-t-Butyl-5-trifluoromethyl)-phenyl-3α,4α-epoxy-6-nitrilo-5-oxo-5,6-secoandrostane (92 mg, 0.17 mmol), as prepared in example 12, 1,2-bis(diphenylphosphino)ethane (3 mg, 0.009 mmol) in anhydrous THF (0.4 mL) under a nitrogen atmosphere is added tetrakis(triphenylphosphine)palladium (0) (10 mg, 0.009 mmol). The resulting mixture is heated under reflux for 18 h then allowed to cool to ambient temperature and concentrated. The residue is purified by silica gel column chromatography using MeOH—CHCl$_3$1:20 as eluent to afford the desired diketone 17β-N-(2-t-Butyl-5-triflouoromethyl)-phenyl-3,5-dioxo-6-nitrilo-5,6-secoandrostane: $^1$H NMR (400 MHz, CDCl$_3$) δ8.10 (s, 1H), 7.48 (d, J=7.2 Hz, 1H), 7.36 (d, J=7.0 Hz, 1H), 7.28 (s, 1H), 4.25 (d, J=17.4 Hz, 1H), 3.45 (dd, J=17.4 and 1.4 Hz, 1H), 2.65 (dd, J=17.9 and 3.5 Hz, 1H), 2.60–1.50 (m, 16H), 1.44 (s, 9H), 1.14 (s, 3H), 0.91 (s, 3H).

Example 14

17β-N-(2-t-Butyl-5-triflouoromethyl)phenyl-3-oxo-6-amido-5-methoxy-5,6 -secoandrost-4-ene; 17β-N-(2-t-Butyl-5-trifluoromethyl)phenyl-5-oxo-6-amido-3 -methoxy-5,6-secoandrost-3-ene A suspension of 17β-N-(2-t-Butyl-5-trifluoromethyl)-phenyl-3,5-dioxo-6 -nitrilo-5,6-secoandrostane (100 mg, 0.184 mmol), as prepared in example 13, in diethylether-MeOH 3:1 (4 mL) is magnetically stirred at 0° C. HCl gas is bubbled through the mixture until it becomes saturated (ca. 30 min). The resulting clear solution is allowed to warm to ambient temperature, and stirred at that temperature for 16 h. The solution is then concentrated in vacuo, the solid residue is dissolved in CH$_2$Cl$_2$ (10 mL) and 1N NaOH (10 mL) is added. The two phase mixture is rapidly stirred for 15 min, the phases separated, the aqueous layer is extracted with CH$_2$Cl$_2$ (2×10 mL), and the combined organic layers are dried over Na$_2$SO$_4$ and concentrated. The residue is purified by silica gel column chromatography using MeOH—CHCl$_3$ 20:1 as eluent to afford 17β-N-(2-t-Butyl-5 -trifluoromethyl)phenyl-3-oxo-6-amido-5-methoxy-5,6-secoandrost-4-ene: $^1$H NMR (400 MHz, CDCl$_3$) δ8.08 (br s, 1H), 7.47 (d, J=8.4 Hz, 1H), 7.33 (dd, J=8.3 and 1.3 Hz, 1H), 7.23 (s, 1H), 5.47 (br s 1H), 5.40 (br s, 1H), 5.26 (s, 1H), 3.64 (s, 3H), 2.44–1.77 (m, 14H), 1.70–1.40 (m, 4H), 1.42 (s, 9H), 1.37 (s, 3H), 0.85 (s, 3H).

Example 15

17β-N-(2-t-Butyl-5-trifluoromethyl)-phenyl-6-azaandrost-4-en-3-one

A magnetically stirred suspension of 17β-N-(2-t-Butyl-5 -trifluoromethyl)phenyl-3-oxo-6-amido-5-methoxy-5,6-secoandrost-4-ene (49 mg, 0.085 mmol), as prepared in example 14, and PhI(OH)OTs (35 mg, 0.089 mmol) in CH$_3$CN—H$_2$O1:1 (1.0 mL) is heated under a nitrogen atmosphere for 2 h. The resulting solution is allowed to cool to ambient temperature, diluted with CH$_2$Cl$_2$ (10 mL), washed with 1N HCl (10 mL), followed by 1N NaOH (10 mL) and concentrated. The residue is purified by silica gel column chromatography using MeOH—CHCl$_3$1:20 as eluent to afford of 17β-N-(2-t-Butyl-5-trifluoromethyl)-phenyl-6-azaandrost-4-en-3-one: $^1$H NMR (400 MHz, CDCl$_3$) δ8.11 (br s, 1H), 7.49 (d, J=8.3 Hz, 1H), 7.36 (dd, J=8.4 and 1.4 Hz, 1H), 7.26 (s, 1H), 5.27 (s, 2H), 3.35 (ddd, J=11.5, 5.6 and 2.3 Hz, 1H), 2.88 (t, J=11.2 Hz, 1H), 2.50–1.80 (m, 10H), 1.69 (m, 3H) 1.55–1.40 (m, 2H), 1.44 (s, 9H), 1.32 (s, 3H), 1.25 (m, 1H), 0.91 (s, 3H).

Example 16

17β-Carbomethoxy-3β,5α,6β-trihydroxy-androstane

A suspension of 17β-carbomethoxy-3β-hydroxy-5-androstene (172 g, 0.5 mol, as prepared in Rasmusson et al., *Journal of Medicinal Chemistry* 1984, 27, 1690, incorporated herein by reference) in 1.7 L of 96% formic acid is heated to about 77° C. over ca. 20 min with stirring. A dark brown solution formed by the time the temperature reached 50° C. The solution is stirred an additional 10 minutes at about 77° C. then the heating mantle is removed and the reaction is allowed to cool. When the internal temperature had reached about 49° C., crystals began to precipitate from the reaction mixture. The reaction is allowed to cool to 25° C. and then placed in a water bath. To the reaction mixture is added 30% hydrogen peroxide (200 mL) over a 5 min period. The internal temperature gradually climbed to 33° C. over about 20 min. The solids had mostly dissolved by this time. The reaction mixture is allowed to stir for 8 h at ambient temperature. The reaction is treated with 3 L of boiling water with stirring. The internal temperature of the reaction mixture reached 67° C. after addition of the hot water. The resulting mixture is stirred while cooling to ambient temperature. The white solid is collected by filtration, dried briefly, dissolved in 2 L of methanol and the solution treated with 200 mL of 25% sodium hydroxide. The reaction mixture is warmed to 70° C. until a solution formed, acidified with 1N hydrochloric acid, and diluted with 200 mL of water. The mixture is stirred while allowing to cool to ambient temperature, and then further cooled in an ice bath for 2 h. The white solid that precipitated is collected by filtration, washed several times with water, and dried to afford 17β-carbomethoxy-3β,5α,6β-trihydroxy-androstane as a white solid, mp 266°–268° C. Anal. Calcd. for C$_{21}$H$_{34}$O$_5$: C, 68.82; H, 9.35. Found: C, 68.79; H, 9.45.

Example 17

17β-Carbomethoxy-6-oxo-3β,5α-dihydroxyo-androstane

A suspension of 17β-Carbomethoxy-3,β,5α,6β-trihydroxy-androstane (43.5 g, 0.24 mol), as prepared in example 16, in 450 mL of dioxane is diluted with 50 mL of water, and maintained at 25° C. by means of an external cooling bath. To this suspension is added N-bromosuccinimide (22.5 g, 0.25 mol). The mixture is stirred for 8 h. The mixture is cooled in an ice bath and the solid collected by filtration, washed with 50% methanol/water, and air dried to afford 17β-carbomethoxy-6-oxo-3β,5α-dihydroxy-androstane as a white solid, mp 258°–260° C. Anal. Calcd. for C$_{21}$H$_{32}$O$_5$: C, 69.20; H, 8.85. Found: C, 69.38; H, 8.92.

Example 18

17β-Carbomethoxy-6-oximino-3β,5α-dihydroxyandrostane

A suspension of 17β-Carbomethoxy-6-oxo-3β,5α-dihydroxy-androstane, 8 g, as prepared in example 17, hydroxylamine hydrochloride (12 g) and sodium acetate trihydrate (16 g) in ethanol (100 mL) is heated at reflux for 1 h. The reaction mixture is cooled to ambient temperature and filtered to afford 17β-carbomethoxy-6-oximino-3β,5α-dihydroxyandrostane as a white solid, mp 234°–237° C. dec. Anal. Calcd. for C$_{21}$H$_{33}$NO$_5$.H$_2$O: C, 63.34; H, 8.88; N, 3.53. Found: C, 62.91; H, 8.98; N, 3.27.

Example 19

17β-Carbomethoxy-3β-hydroxy-6-nitrilo-5-oxo-5,6-secoandrost-3-ene

A solution of 17β-Carbomethoxy-6-oximino-3β,5α-dihydroxyandrostane, 3.8 g, 10 mmol, as prepared in example 18, and hexachlorocyclotriphosphazene (3.48 g, 10 mmol)

in tetrahydrofuran (50 mL) is treated with pyridine (8 g, 100 mmol) while stirring at ambient temperature. The mixture is allowed to stir at ambient temperature overnight. The white precipitate (pyridine hydrochloride) is removed by filtration, and the filtrate is concentrated under reduced pressure. The residue is taken up in toluene, washed several times with water, dried over sodium sulfate, filtered, and concentrated to give crude 17β-carbomethoxy-3β-hydroxy-6-nitrilo-5-oxo-5,6-secoandrost-3-ene as a white foam. $^1$H NMR (400 MHz, CDCl$_3$) δ4.56 (br s, 1H), 3.68 (s, 3H), 3.47 (dd, J=17.8 and 3.8 Hz, 1H), 2.55 (dd, J=17.8 and 3.8 Hz, 1H), 2.56–2.50 (m, 1H), 2.45 (t, J=9.1 Hz, 1H), 2.2–2.05 (m, 4H), 1.95–1.4 (m, 10H), 1.3–1.18 (m, 2H), 0.99 (s, 3H), 0.68 (s, 3H).

Example 20

17β-Carbomethoxy-3,5-dioxo-6-nitrilo-5,6-secoandrostane

A mixture of 17β-Carbomethoxy-3β-hydroxy-6-nitrilo-5-oxo-5,6-secoandrost-3-ene (0.36 g, 1 mmol) as prepared in example 19, pyridinium dichromate (0.51 g, 1.5 mmol), and methylene chloride (5 mL) is stirred at ambient temperature for 24 h. The reaction mixture is filtered through a plug of silica gel and the silica is washed with ethyl acetate. The filtrates were concentrated to give 17β-carbomethoxy-3,5-dioxo-6-nitrilo-5,6-secoandrostane as a slightly colored foam which was identical ($^1$H NMR, and TLC) to the compound prepared in example 4.

What is claimed is:

1. A method of synthesizing a compound of Formula (I)

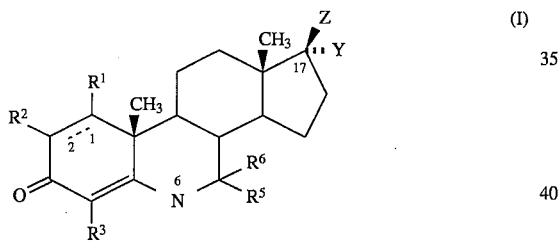

(I)

which comprises annulating a compound of Formula (VI)

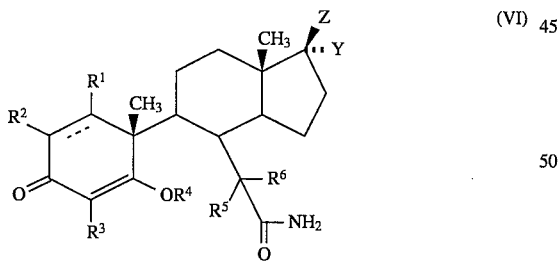

(VI)

wherein:
R$^1$ and R$^2$ represent;
  i) independently H or alkyl and the bond between carbons 1 and 2 is a single bond or a double bond, or
  ii) taken together are a —CH$_2$— group to form a cyclopropane ring, and the bond between the carbons bearing R$^1$ and R$^2$ is a single bond;
R$^3$ represents H, —Alk$^1$—H optionally substituted with one or more halogen atoms, cycloalkyl, cycloalkyl-alkyl, halogen, —(Alk$^1$)$_n$—CO$_2$H, —(Alk$^1$)$_n$—CO$_2$R$^8$, —(Alk$^1$)$_n$—Ar$^1$, —(Alk$^1$)$_n$—CONR$^9$R$^{10}$, —(Alk$^1$)$_n$—NR$^9$R$^{10}$, —(ALk$^1$)$_n$—S(O)$_r$R$^8$, —(Alk$^1$)$_n$—CN, —(Alk$^1$)-hydroxy, or —(Alk$^1$)$_n$—OR$^8$;

wherein:
Alk$^1$ represents alkylene, alkenylene or alkynylene;
n represents 0 or 1
r represents 0, 1 or 2;
R$^4$ represents alkyl;
R$^8$ represents —Alk$^1$—H, —(Alk$^1$)$_n$—Ar$^1$ or cycloalkyl;

wherein:
—Ar$^1$ represents an aryl or heteraryl group of 6 to 14 atoms;
R$^9$ and R$^{10}$ represent independently H, —Alk$^1$—H or cycloalkyl;
Y represents H or hydroxy;
Z represents alkyl, —(Alk$^2$)$_n$—COR$^{11}$, —(Alk$^2$)$_n$—CO$_2$R$^{11}$, —(Alk$^2$)$_n$—CO—thiopyridinyl or —(Alk$^2$)$_n$—CONR$^{12}$R$^{13}$, wherein:
Alk$^2$ represents, (C$_{2-12}$) alkylene, (C$_{2-12}$) alkenylene or (C$_{2-12}$) alkynylene;
R$^{11}$ represents H, alkyl, —Alk$^1$—H, cycloalkyl or adamantyl;
R$^{12}$ and R$^{13}$ represent,
  i) independently, H, —Alk$^2$—H, cycloalkyl, alkoxy, adamantyl,—Ar$^1$, —Ar$^1$-alkyl-perhaloalkyl, benzyl, diphenylmethyl, triphenylmethyl or —(Alk$^1$)$_n$-norbornyl; or
  ii) taken together with the linking nitrogen to form a 4 to 8 atom heterocyclic group

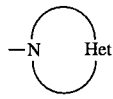

wherein:
Het represents —O—, —CH$_2$—, —S(O)$_r$—, —NH— or —N(Alk$^1$—H)—; optionally substituted with one or more alkyl groups;
R$^5$ and R$^6$ represent H or alkyl; or the pharmaceutically acceptable salt or solvate thereof.

2. The method of claim 1,
wherein:
R$^1$, R$^2$, R$^3$, R$^5$, R$^6$ and Y represent H,
R$^4$ represents methyl,
Z represents —(Alk$^2$)$_n$—CO$_2$R$^{11}$ or —(Alk$^2$)$_n$—CONR$^{12}$R$^{13}$
wherein:
n represents 0 and R$^{11}$ represents methyl, R$^{12}$ represents
H and R$^{13}$ represents —Ar$^1$-alkyl-perhaloaklyl, and
wherein:
—Ar$^1$ represents (2-tert-butyl-5-trifluoromethyl)phenyl.

3. The method of claim 2 wherein the annulating agent is selected from the group consisting of: bis(trifluoroacetoxy)iodobezene, hydroxy(tosyloxy)iodobezene, sodium hypochlorite and sodium hypobromate.

4. A method of synthesizing a compound of Formula (I)

(I)

which comprises the steps of:
i) annulating a compound of Formula (VIa)

(VIa)

and ii) hydrolysing a compound of Formula (IX)

(IX)

wherein:
$R^1$ and $R^2$ represent;
i) independently H or alkyl and the bond between carbons 1 and 2 is a single bond or a double bond, or
ii) taken together are a —$CH_2$— group to form a cyclopropane ring, and the bond between the carbons bearing $R^1$ and $R^2$ is a single bond; $R^3$ represents H, —$Alk^1$—H optionally substituted with one or more halogen atoms, cycloalkyl, cycloalkyl-alkyl, halogen, —$(Alk^1)_n$—$CO_2H$, —$(Alk^1)_n$—$CO_2R^8$, —$(Alk^1)_n$—$Ar^1$, —$(Alk^1)_n$—$CONR^9R^{10}$, —$(Alk^1)_n$—$NR^9R^{10}$, —$(Alk^1)_n$—$S(O)_rR^8$, —$(Alk^1)_n$—CN, —$(Alk^1)$-hydroxy, or —$(Alk^1)_n$—$OR^8$;

wherein:
$Alk^1$ represents alkylene, alkenylene or alkynylene;
n represents 0 or 1
r represents 0, 1 or 2;
$R^4$ represents alkyl;
$R^8$ represents —$Alk^1$—H, —$(Alk^1)_n$—$Ar^1$ or cycloalkyl;

wherein:
—$Ar^1$ represents an aryl or heteraryl group of 6 to 14 atoms;
$R^9$ and $R^{10}$ represent independently H, —$Alk^1$—H or cycloalkyl;
Y represents H or hydroxy;
Z represents alkyl, —$(Alk^2)_n$—$COR^{11}$, —$(Alk^2)_n$—$CO_2R^{11}$, —$(Alk^2)_n$—CO—thiopyridinyl or —$(Alk^2)_n$—$CONR^{12}R^{13}$, wherein:
$Alk^2$ represents, ($C_{2-12}$) alkylene, ($C_{2-12}$) alkenylene or ($C_{2-12}$) alkynylene;
$R^{11}$ represents H, alkyl, —$Alk^1$—H, cycloalkyl or adamantyl;
$R^{12}$ and $R^{13}$ represent,
i) independently, H, —$Alk^2$—H, cycloalkyl, alkoxy, adamantyl, —$Ar^1$, —$Ar^1$-alkyl-perhaloalkyl, benzyl, diphenylmethyl, triphenylmethyl or —$(Alk^1)_n$-norbornyl; or
ii) taken together with the linking nitrogen to form a 4 to 8 atom heterocyclic group wherein:
Het represents —O—, —$CH_2$—, —$S(O)_r$—, —NH— or —$N(Alk^1$—H)—;
optionally substituted with one or more alkyl groups;
$R^5$ and $R^6$ represent H or alkyl; or
the pharmaceutically acceptable salt or solvate thereof.

5. The method of claim 4,
wherein:
$R^1$, $R^2$, $R^3$, $R^5$, $R^6$ and Y represent H,
$R^4$ represents methyl;
Z represents —$(Alk^2)_n$—$CO_2R^{11}$ or —$(Alk^2)_n$—$CONR^{12}R^{13}$ wherein:
n represents 0 and $R^{11}$ represents methyl, $R^{12}$ represents
H and $R^{13}$ represents —$Ar^1$-alkyl-perhaloaklyl, wherein:
—$Ar^1$ represents (2-tert-butyl-5-trifluoromethyl)phenyl.

6. The method of claim 5 wherein the annulating agent in step i) is selected from the group consisting of: bis(trifluoroacetoxy)iodobezene, hydroxy(tosyloxy)iodobezene, sodium hypochlorite and sodium hypobromate.

7. The method of claim 6 wherein the hydrolysing agent in step ii) is a mild acid selected from the group consisting of: silica gel, Amberlyst® 15 ion-exchange resin and Dowex® 50 W ion-exchange resin.

* * * * *